US007942859B2

(12) United States Patent
Nakajima et al.

(10) Patent No.: US 7,942,859 B2
(45) Date of Patent: May 17, 2011

(54) DISPOSABLE WEARING ARTICLE

(75) Inventors: Kaiyo Nakajima, Kagawa-ken (JP); Naoko Takada, Kagawa-ken (JP); Hironao Minato, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 732 days.

(21) Appl. No.: 11/340,564

(22) Filed: Jan. 27, 2006

(65) Prior Publication Data

US 2006/0173435 A1 Aug. 3, 2006

(30) Foreign Application Priority Data

Jan. 28, 2005 (JP) .................................. 2005-21890

(51) Int. Cl.
*A61F 13/15* (2006.01)
*A61F 13/20* (2006.01)

(52) U.S. Cl. .......... 604/385.27; 604/385.24; 604/385.01

(58) Field of Classification Search ............. 604/385.19, 604/385.24–385.29
See application file for complete search history.

(56) References Cited

U.S. PATENT DOCUMENTS

| | | | | |
|---|---|---|---|---|
| 4,743,241 A * | 5/1988 | Igaue et al. | ............... | 604/385.26 |
| 4,990,147 A * | 2/1991 | Freeland | ................... | 604/385.22 |
| 5,207,663 A * | 5/1993 | McQueen | ................ | 604/385.05 |
| 5,576,091 A * | 11/1996 | Zajaczkowski et al. | ....... | 428/192 |
| 5,672,166 A * | 9/1997 | Vandemoortele | ........ | 604/385.28 |
| 5,716,351 A * | 2/1998 | Roe et al. | ................. | 604/385.21 |
| 5,746,730 A * | 5/1998 | Suzuki et al. | ............ | 604/385.26 |
| 5,779,690 A * | 7/1998 | Gustafsson et al. | ..... | 604/385.19 |
| 5,792,130 A * | 8/1998 | Widlund et al. | ......... | 604/385.01 |
| 5,817,086 A * | 10/1998 | Kling | ..................... | 604/385.19 |
| 5,830,203 A * | 11/1998 | Suzuki et al. | ............ | 604/385.19 |
| 5,928,211 A * | 7/1999 | Gustafsson et al. | ..... | 604/385.22 |
| 5,957,907 A * | 9/1999 | Sauer | ....................... | 604/385.24 |
| 6,010,490 A * | 1/2000 | Freeland et al. | ......... | 604/385.19 |
| 6,120,485 A * | 9/2000 | Gustafsson et al. | ..... | 604/385.19 |
| 6,123,692 A * | 9/2000 | Guidotti et al. | .......... | 604/385.01 |
| 6,152,907 A * | 11/2000 | Widlund et al. | ......... | 604/385.08 |
| 6,152,908 A * | 11/2000 | Widlund et al. | ......... | 604/385.19 |
| 6,328,724 B1 * | 12/2001 | Ronnberg et al. | ........ | 604/385.24 |
| 6,716,204 B1 * | 4/2004 | D'Acchioli et al. | ...... | 604/385.19 |
| 6,960,197 B1 * | 11/2005 | Gustafsson et al. | .......... | 604/348 |
| 7,037,299 B2 * | 5/2006 | Turi et al. | .................. | 604/385.19 |
| 7,175,613 B2 * | 2/2007 | Sugiyama et al. | ....... | 604/385.14 |
| 2003/0220623 A1 * | 11/2003 | Sugiyama et al. | ............. | 604/378 |

(Continued)

FOREIGN PATENT DOCUMENTS

EP 1 057 463 A2 12/2000

(Continued)

*Primary Examiner* — Michele Kidwell
(74) *Attorney, Agent, or Firm* — Lowe, Hauptman, Ham & Berner, LLP

(57) ABSTRACT

A wearing article includes a flexible chassis and a semi-rigid absorbent panel laid on inner surface of the chassis. A liner defining an innermost layer of the chassis is bonded to the absorbent panel in a fixed zone defined in a crotch region. A passage is formed through the liner at a position put aside from the fixed zone toward a rear waist region to guide feces through this passage. A first elastic member extends along a peripheral edge of the passage so as to be stretchable and contractible. A second elastic member and a third elastic member are paired and laid outside opposite side edges of the passage so as to be stretchable and contractible in a longitudinal direction in a vicinity of the passage.

21 Claims, 8 Drawing Sheets

U.S. PATENT DOCUMENTS

2006/0058766 A1 * 3/2006 Mueller et al. ............ 604/385.19

FOREIGN PATENT DOCUMENTS

| EP | 1 080 707 | 3/2001 |
| EP | 1 234 563 A2 | 8/2002 |
| JP | 2572744 | 10/1996 |
| JP | 2880191 | 1/1999 |
| JP | 2003-204988 | 7/2003 |
| WO | 01/01907 | 1/2001 |
| WO | WO 0224130 A1 * | 3/2002 |

* cited by examiner

DISPOSABLE WEARING ARTICLE

RELATED APPLICATIONS

The present application is based on, and claims priority from, Japanese Application Number 2005-21890, filed Jan. 28, 2005, the disclosure of which is hereby incorporated by reference herein in its entirety.

BACKGROUND OF THE INVENTION

The present invention relates to a disposable wearing article and more particularly to a disposable wearing article adapted to prevent bodily waste from clinging to the wearer's body.

Japanese Patent Publication No. 2572744B proposed a disposable diaper which is provided, in a crotch region of a topsheet and at a forward position, with an opening and further with elastic members extending in the longitudinal direction. Furthermore, Japanese Patent Publication No. 2880191B proposed a disposable diaper provided, on its liner and at a rear position, with an opening and further with contractile means spaced from the this opening in the longitudinal direction. In these disposable diapers, the topsheet or the liner is normally biased to be sufficiently lifted above the underlying absorbent panel so as to reliably receive bodily waste through the opening.

In the disposable diaper disclosed in JP2572744B, the location at which the topsheet is formed with the opening is not limited to, i.e., may be forward of the vicinity of the wearer's anus. Consequentially, there is a serious apprehension that the wearer's skin might be contaminated not only around the anus but also around the external genitalia. In the disposable diaper disclosed in JP2880191B the entire area of the liner is lifted up and the front zone with the opening also comes in direct contact with the wearer's external genitalia. Consequentially, comfort to the wearer may be deteriorated or the wearer's skin may suffer from rash. In addition, when a large amount of urine is discharged at once, the amount of urine may exceed the capacity of the disposable diaper and may lead to leak of urine.

SUMMARY OF THE INVENTION

In view of the problem as has been described above, it is an object of the present invention to provide a disposable wearing article improved to protect the wearer's external genitalia from being contaminated with feces without deterioration of a feeling to wear the article and/or reduction of a urine containing capacity.

The present invention in directed to a disposable wearing article comprising: a longitudinal direction; a transverse direction; a front waist region; a rear waist region; a crotch region extending between the front and rear waist region; a flexible chassis; a semi-rigid absorbent panel laid on an inner surface of the chassis; the chassis having an outermost layer, an innermost layer, a backsheet defining the outermost layer and a liner defining the innermost layer; the liner being fixed to the absorbent panel in a fixed zone defined substantially in a middle region of the crotch region as viewed in the transverse direction and extending in the transverse direction; a passage formed through the liner at a region put aside from the fixed zone toward the rear waist region to guide feces through the passage; a first elastic member extending along a peripheral edge of the passage so as to be stretchable and contractible; and a second elastic member and a third elastic member which are paired and laid outside opposite side edges of the passage so as to be stretchable and contractible in the longitudinal direction in a vicinity of the passage; whereby the liner is lifted off from the absorbent panel in the region put aside from the fixed zone toward the rear waist region so as to form a barrier rising up along the fixed zone as the second and third elastic members contract.

The passage comes close to the wearer's anus as the liner is lifted off from the absorbent panel in the region put aside from the fixed zone toward the rear waist region and, in this state, the liner reliably guides feces through the passage. In addition, the liner forms the barrier rising up along the fixed zone and the upper edge of this barrier is held in a close contact with a wearer's perineum during use of the wearing article so that the barrier can reliably block feces and protect the wearer's external genitalia from being contaminated with feces. The liner is fixed to the absorbent panel along the fixed zone lying in the crotch region and the chassis is kept reliably spaced from the wearer's skin in the front waist region during use of the wearing article. Consequentially, there is no anxiety that the wearer might experience any uncomfortable feeling and/or suffer from rash. It is unlikely that urine leak might occur even if a large amount of urine is discharged at once.

Configuration and size of the passage are not particularly specified so far as feces can pass through the passage. For example, the passage may be implemented in the form of a slit extending in the longitudinal or transverse direction or an opening formed by partially cutting out the liner. While the passage may be appropriately positioned so that the passage falls in line with the wearer's anus as the liner is lifted off from the absorbent panel, the passage is preferably formed at the position put aside from the crotch region toward the rear waist region substantially along the middle of the chassis as viewed in the transverse direction.

In the case of the liner provided along the peripheral edge of the passage with the first elastic member attached thereto in a stretchable and contractible fashion, the peripheral edge of the passage is sufficiently reinforced to keep the passage in an opened state. The first elastic member well follows the wearer's movement to be stretched or contracted so that the passage can be kept opened toward the wearer's anus.

In the case of the liner provided in the vicinity of the passage, in addition to the first elastic member, with the paired second and third elastic members extending on the transversely opposite sides of the passage so as to be stretchable and contractible in the longitudinal direction, contraction of these second and third elastic members causes the liner to be lifted off from the absorbent panel and thereby causes the passage to get nearer to the wearer's anus. In this way, it is facilitated to guide feces through the passage. At the same time, the liner rises up along the fixed zone to form the barrier having its upper edge coming in close contact with the wearer's perineum. Consequentially, it is ensured that the barrier reliably blocks feces even if feces moves forward on the wearer's skin.

While the positions at which the front and rear end segments of the second and third elastic members terminate are not particularly specified, the rear end segments of these elastic members preferably terminate at least behind the longitudinal middle of the passage and, more preferably, behind the rearmost edge of the passage to maintain the passage as a whole closer to the wearer's anus. These second and third elastic members preferably extend forward in the longitudinal direction in a stretchable and contractible fashion at least to the foremost edge of the passage and, more preferably, at least to the fixed zone to ensure that the upper edge of the barrier rising more reliably comes in close contact with the wearer's perineum and this barrier effectively blocks feces.

In the case of these second and third elastic members extending in a stretchable and contractible fashion in the longitudinal direction so as to describe curves which are convex toward the passage, contraction of these second and third elastic members prevents the opening's dimension of the passage in the transverse direction from being narrowed and thereby allows feces to be reliably guided through the passage.

While the liner may be liquid-pervious or liquid-resistant, the liner is preferably liquid-pervious substantially in the front half of the chassis facing the wearer's urethra and preferably liquid-resistant substantially in the rear half of the chassis facing the wearer's anus. Preferably, the first liner has a flexibility lower than that of the second liner. The liner preferably comprises the first liner extending substantially in the front half of the chassis and the second liner provided separately of the first liner and extending substantially in the rear half of the chassis. In this way, the property of the chassis is easily differentiated between the front half and the rear half as has previously been described.

In the case of the chassis provided on the opposite side edges thereof with a pair of the barrier cuffs extending in the longitudinal direction, these barrier cuffs also function against bodily waste.

With the disposable wearing article according to the present invention, the passage formed so as to extend through the liner closely faces the wearer's anus and the upper edge of the barrier rising comes in contact with the wearer's perineum. In this way, feces can be reliably guided through the passage and the wearer's external genitalia can be protected from being contaminated with feces. In the region aside from the fixed zone toward the front waist region, a space is maintained between the chassis and the wearer's skin adequate to improve a feeling to wear, on one hand, to prevent leakage of urine even if a large amount of urine is discharged at once.

The other arrangements as well as features will be understood from detailed description of the embodiments described hereunder. However, the present invention is not limited to these embodiments.

DETAILED DESCRIPTION OF THE PREFERRED EMBODIMENTS

Details of a disposable wearing article according to the present invention will be more fully understood from the description of the disposable diaper as typical embodiment given hereunder with reference to the accompanying drawings.

First Embodiment

Figure 1:
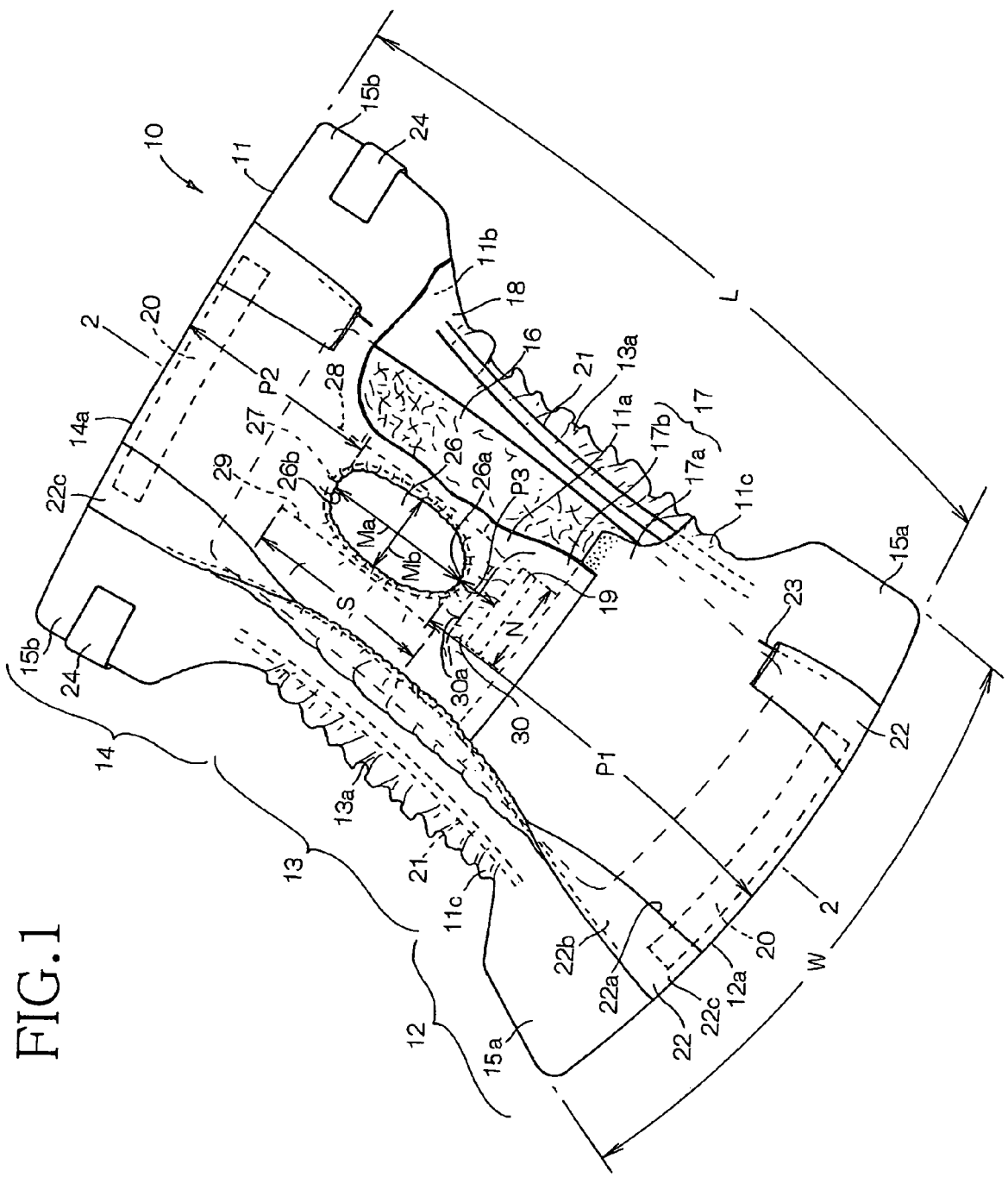
FIG. 1 is a partially cutaway plan view showing a disposable diaper according to the first embodiment of this invention.
Figure 2:
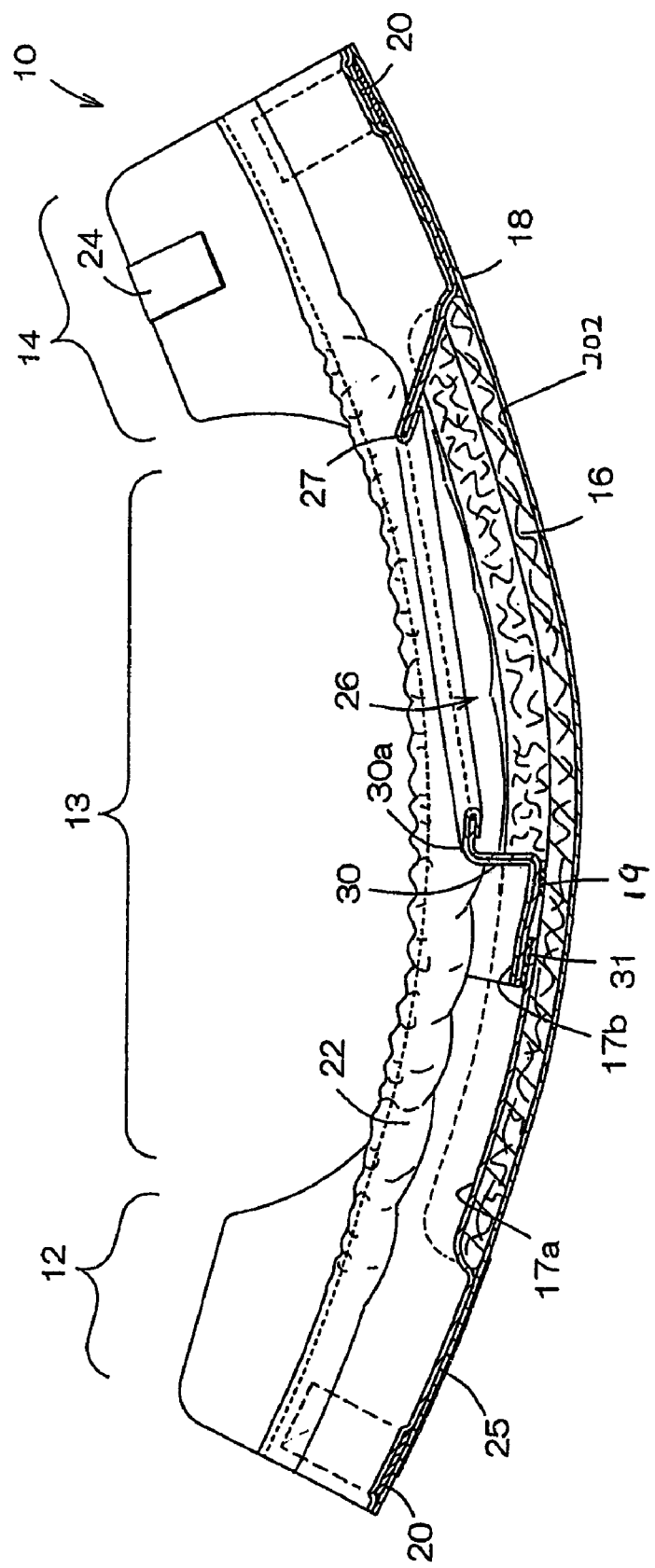
FIG. 2 is a sectional view taken along a line II-II in FIG. 1.

FIG. 1 is a partially cutaway perspective view showing an open-type disposable diaper 10 according to a first embodiment of the present invention and FIG. 2 is a sectional view taken along a line 2-2 in FIG. 1.

The disposable diaper 10 has a longitudinal direction and a transverse direction. The diaper 10 is symmetric about a center line 2 extending in the longitudinal direction and bows in the longitudinal direction as viewed in FIG. 1. The disposable diaper 10 generally includes a chassis 11 having a front waist region 12, a rear waist region 14, and a crotch region 13 extending between these two waist regions 12, 14 and a semi-rigid absorbent panel 16 laid on an inner surface 202 of an outer layer of this chassis 11.

The chassis 11 has a middle portion as viewed in the longitudinal direction which is constricted so as to provide the chassis 11 with an hourglass-like shape as a whole. The chassis 11 has an innermost layer 11a and an outermost layer 11b and includes a liner 17 defining the innermost layer 11a and a backsheet 18 defining the outermost layer 11b.

The liner 17 includes a first liner 17a laid in a substantially front half section of the chassis 11 and formed by a single sheet and a second liner 17b laid in a substantially rear half of the chassis 11 and formed by two sheets. The liner 17 is bonded along its outer edge to the backsheet 18. In addition, the liner 17b is fixed to the absorbent panel 16 along a fixed zone 19 located at a transverse middle of the crotch region 13 so as to extend in the transverse direction. It is not essential to fix the second liner 17b directly to the absorbent panel 16 at the fixed zone 19 and it is possible without departing from the scope of the invention to fix this second liner 17b to the absorbent panel 16 by the intermediary of the first liner 17a. In the disposable diaper according to this embodiment, the second liner 17b overlaps the first liner 17a from above in the crotch region 13 and these overlapped portions are bonded to each other, as will be seen in FIG. 2. Preferably, the first liner 17a has a flexibility lower than that of the second liner 17b.

The first liner 17a is liquid-pervious and made of well known thermoplastic synthetic fibrous nonwoven fabric. The second liner 17b is liquid-resistant and air-permeable and made of well known thermoplastic synthetic fibrous nonwoven fabric. The thermoplastic synthetic fibrous nonwoven fabric may be selected from, for example, those made from polyolefin-, polyester- and polyamide-based synthetic resin.

The backsheet 18 is made of well known liquid-impervious thermoplastic synthetic fibrous nonwoven fabric or well known liquid-resistant thermoplastic film. The film may be selected from, for example, polyolefin-based plastic, more preferably, breathable but liquid-impervious plastic film obtained by uniaxial or biaxial orientation of synthetic resin film containing inorganic microparticles such as calcium carbonate or barium sulfate.

The absorbent panel 16 is a mixture of fluff pulp, superabsorbent polymer particles and, if desired, thermoplastic synthetic fibers appropriately compressed together. Consequentially, the absorbent panel 16 is semi-rigid with respect to the flexible chassis. Preferably, this compressed mixture is entirely wrapped with a liquid-diffusive sheet (not shown) such as a tissue paper or nonwoven fabric for its shape retention and desired absorbability. While FIG. 1 shows the absorbent panel 16 of a rectangular shape, the panel 16 may also have an hourglass-like shape similar to the chassis 11 having its middle portion constricted so as to provide the chassis 11 with the hourglass-like shape. As will be seen in FIG. 1, the absorbent panel 16 in the disposable diaper 10 according to this embodiment, the absorbent panel 16 has a uniform thickness over all. Preferably, a section of the absorbent panel 16 extending in the rear waist region 14 may include thinner zones depressed toward the backsheet 18 or partially cut off to improve a feces retaining capacity.

Along respective front and rear ends 12a, 14a of the front and rear waist regions 12, 14, waist-surrounding elastic members 20, 20 are attached to the inner surface 202 of the outer layer of the chassis 11 in a stretchable/contractible manner. Along opposite side edges 13a, 13a of the crotch region 13, leg-surrounding elastic members 21, 21 are attached to the inner surface 202 of the outer layer of the chassis 11 in a stretchable/contractible manner and the chassis 11 is provided on its inner surface with a pair of gasket cuffs 11c, 11c extending in the longitudinal direction. Barrier cuffs 22, 22 are laid on upper surfaces of the respective gasket cuffs 11c, 11c. The barrier cuffs 22 extend to the outer edge of the backsheet 18 and are placed thereupon. Each of the barrier cuffs 22 has a proximal section 22a forming the gasket cuff 11c and a distal section 22b collapsed outward in the transverse direction. In such a collapsed state, longitudinally opposite ends 22c, 22c are fixed to the gasket cuffs 11c, 11c, respectively. The barrier cuffs 22 are provided with cuff elastic members 23 attached thereto, respectively, in a manner that these elastic members 23 are stretchable and contractible in longitudinal direction thereof. Contraction of these cuff elastic members 23 causes the barrier cuffs 22 to rise up with respect to the upper surface of the chassis 11 and cooperate with the respective gasket cuffs 11c to form barriers against bodily waste. The barrier cuffs 22 are made of well known liquid-resistant thermoplastic synthetic fibrous nonwoven fabric. The thermoplastic synthetic fibrous nonwoven fabric maybe selected from, for example, those made from polyolefin-, polyester- and polyamide-based synthetic resin.

A pair of tape fasteners 24, 24 used to connect the front and rear waist regions 12, 14 with each other are attached to transversely opposite side edges 15b, 15b of the chassis 11 in the rear waist region 14. Each of the tape fasteners 24 has a proximal section permanently bonded to the chassis 11 and a distal section coated with a pressure-sensitive adhesive. The front waist region 12 of the chassis 11 is provided with a target tape strip 25 onto which the tape fastener 24 is anchored (See FIG. 2). It should be noted that the disposable diaper 10 may be also in the type-pants (referred to also as "pull-on-type") in which the front and rear waist regions 12, 14 have previously been bonded to each other along the transversely opposite side edges 15a, 15b of these two waist regions, respectively.

The liner 17 has a passage 26 located aside from the fixed zone 19 toward the rear waist region 14 and serving to receive feces, a first elastic member 27 provided so as to be stretchable and contractible along a peripheral edge of the passage 26 and a pair of elastic members, i.e., second and third elastic members 28, 29 attached to the inner surface of the liner 17 on both sides and in the vicinity of the passage 26 so that these second and third elastic members 28, 29 are stretchable and contractible in the longitudinal direction. Contraction of the second and third elastic members 28, 29 causes a region of the liner 17 located aside from the fixed zone 19 toward the rear waist region 14 to be lifted off from the absorbent panel 16 and to form a barrier 30 rising up along the fixed zone 19 (See FIG. 2). An upper edge 30a of this barrier 30 comes in contact with the wearer's perineum. Such disposable diaper 10 ensures that the passage 26 of the liner 17 is aligned with the wearer's anus and thereby reliably guides feces for retention thereof. Should feces move forward on the wearer's skin, it is unlikely that the wearer's external genitalia might be contaminated with feces since the upper edge 30a of the barrier 30 is kept in close contact with the wearer's perineum. The first elastic member may be continuously or intermittently bonded to the liner fully along the peripheral edge of the passage.

With the relevant elastic members being not in a stretched sate, a longitudinal dimension Ma of the passage 26 as measured from a foremost edge 26a to a rearmost edge 26b is preferably in a range of about 8 to about 40% of a longitudinal dimension L of the chassis 11 (for example, in a range of about 38 to about 190 mm with respect to the dimension L of 475 mm). If the dimension Ma is less than 8% of the dimension L, it will be difficult to guide feces through the passage 26. If the dimension Ma exceeds 40% of the dimension L, on the contrary, the passage will face also the wearer's external genitalia and feces may possibly cling to the wearer's external genitalia.

Also with the relevant elastic members being not in a stretched state, a transverse dimension Mb of the passage 26 is preferably in a range of about 5 to about 70 mm. If the dimension Mb is less than about 5 mm, it will be difficult to guide feces through the passage 26. If the dimension Mb exceeds about 70 mm, on the contrary, feces once having been guided through the passage 26 may possibly cling to the wearer's skin and it will be not expected to protect the wearer's external genitalia against being contaminated with feces.

A dimension P1 by which the foremost edge 26a of the passage 26 is spaced from the front end 12a of the chassis 11 is preferably in a range of about 37 to about 57% of the dimension L (for example, in a range of about 180 to about 270 mm with respect to the dimension L of 475 mm). If the dimension P1 is less than about 37% of the dimension L, the passage 26 will rather face the wearer's external genitalia and feces may possibly cling to the wearer's external genitalia. If the dimension P1 exceeds about 57% of the dimension L, on the contrary, it will be difficult for the passage 26 to face the wearer's anus and consequently to guide feces therethrough.

A dimension P2 by which the rearmost edge 26b is spaced from the rear end 14a of the chassis 11 is preferably in a range of about 13 to 33% of the dimension L (for example, in a range of about 60 to about 150 mm with respect to the dimension L of 475 mm). If the dimension P2 is less than about 13% of the dimension L, the rearmost edge 26b of the passage 26 will be excessively aside toward the wearer's back and consequently feces may spread on the wearer's back until feces may leak beyond the chassis 11. If the dimension P2 exceeds about 33% of the dimension L, on the contrary, it will be difficult for the passage 26 to face the wearer's anus and consequently to guide feces therethrough.

By provision of such uniquely arranged passage 26, this disposable diaper 10 ensures that the wearer's external genitalia are more reliably protected against being contaminated with feces.

In the fixed zone 19, the liner 17 and the absorbent panel 16 are bonded to each other by means of a hot melt adhesive 31 (See FIG. 2). The fixed zone 19 is located in a substantially transverse middle of the chassis 11 and a transverse dimension N is preferably 75% or higher of the transverse dimension Mb of the passage 26. If the dimension N is less than 75% of the dimension Mb, a transverse dimension of the barrier 30 will be too small to achieve an expected function for this barrier 30. A dimension P3 as measured from the fixed zone 19 to the foremost edge 26a of the passage 26 corresponding a height of the barrier 30 formed by the liner 17 is preferably in a range of 20 to 60 mm. If the dimension P3 is less than 20 mm, the barrier 30 will not achieve the expected function. If the dimension P3 exceeds 60 mm, on the contrary, the wearer may experience a feeling of incompatibility when the barrier 30 comes in contact with the wearer's skin.

The first elastic member 27 is wrapped with the second liner 17b comprising a pair of sheets and continuously extends along the entire peripheral edge of the passage 26.

The second and third elastic members 28, 29 are laid aside from the first elastic member 27 toward the side edges of the liner 17 and sandwiched between two sheets constituting the second liner 17b. These second and third elastic members 28, 29 extend substantially in parallel to each other in the longitudinal direction from the foremost edge 26a beyond the rearmost edge 26b of the passage 26 in a stretchable and contractible manner. Preferably, the second and third elastic members 28, 29 are spaced from the peripheral edge of the passage 26 by a range of 5 to 30 mm and located so as to intersect a transverse center line of the passage 26. If the second and third elastic members 28, 29 are spaced in the transverse direction from the peripheral edge of the passage 26 by more than 30 mm, stretch stress of these second and third elastic members 28, 29 will not be effectively transmitted to the peripheral edge of the passage 26 and consequently it will be difficult to maintain the passage 26 in an opened state. A longitudinal dimension S of the second and third elastic members 28, 29 is preferably is in a range of 50 to 150% of the longitudinal dimension Ma of the passage 26. If the dimension S is less than 50% of the dimension Ma, it will be difficult for the liner 17 to be lifted off from the absorbent panel 16.

The first, second and third elastic members 27, 28, 29 may be selectively formed by thread-like rubber, flat rubber or the like made from well known material such as natural rubber, synthetic rubber, urethane foam, or the like.

In the disposable diaper according to this embodiment, the first elastic member laid along the peripheral edge of the passage reinforces the peripheral edge of the passage so as to maintain the passage in its opened state. The second and third elastic members respectively laid on transversely opposite sides of the passage cooperated with each other to bias the passage close to the wearer's anus. In addition, these second and third elastic members extend forward so as to be stretchable and contractible in the longitudinal direction at least to the foremost edge of the passage. Consequentially, the passage as a whole inclusive of the foremost edge is biased close to the wearer's anus so as to ensure that feces is reliably guided into the passage as the liner is lifted off from the absorbent panel. Even if feces move forward on the wearer's skin, there is no anxiety that the wearer's external genitalia might be contaminated with feces since the upper edge of the barrier formed by the liner is reliably kept in close contact with the wearer's perineum and blocks feces. The fixed zone of the liner is bonded to the absorbent panel and there is no possibility that the chassis might come in close contact with the wearer's skin in the region of the chassis extending forward from the fixed zone toward the front waist region. In this way, there is unlikely that the wearer might experience uncomfortable feeling and/or a leakage might occur due to a large amount of urine discharged at once.

Second Embodiment

Figure 3:
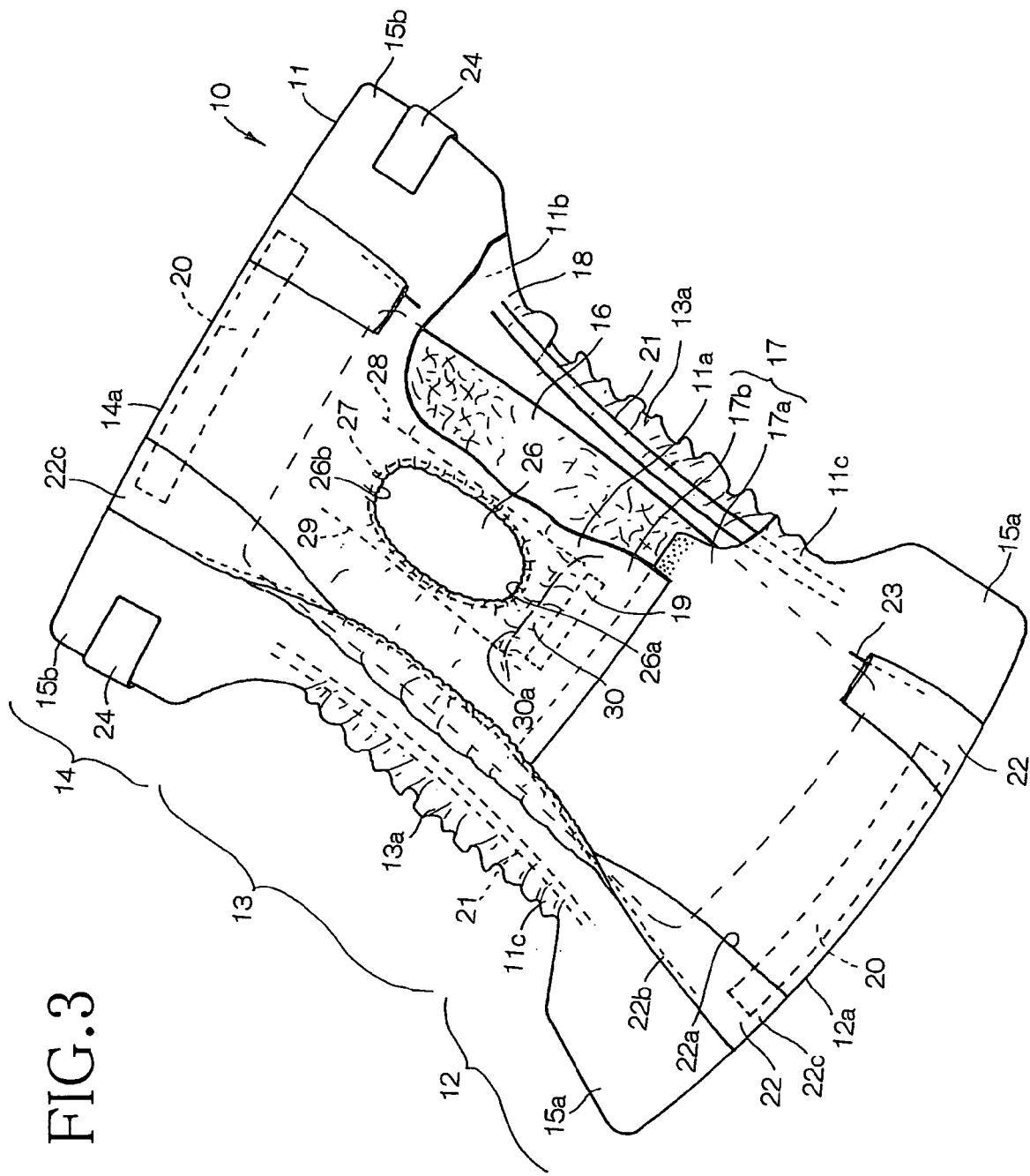
FIG. 3 is a partially cutaway plan view similar to FIG. 1, showing a disposable diaper according to the second embodiment of this invention.

FIG. 3 is a partially cutaway plan view showing a disposable diaper according to the second embodiment of this invention similar to FIG. 1.

Of the disposable diaper according to this second embodiment, the basic members and regions or zones similar to those in the disposable diaper according to the first embodiment are designated by the respectively corresponding reference numerals and not repetitively described.

The disposable diaper according to this second embodiment is distinguished from that according to the first embodiment in that the second and third elastic members 28, 29 extend in the longitudinal direction beyond the foremost edge 26a of the passage 26 to the fixed zone 19.

In the disposable diaper according to this embodiment, the second and third elastic members are relatively long and the liner is correspondingly facilitated to be lifted off. In addition, the second and third elastic members extending so as to stretchable and contractible in the longitudinal direction beyond the fixed zone ensure that the upper edge of the barrier formed by the liner is more reliably held in close contact with the wearer's skin and feces is more effectively blocked thereby.

Third Embodiment

Figure 4:
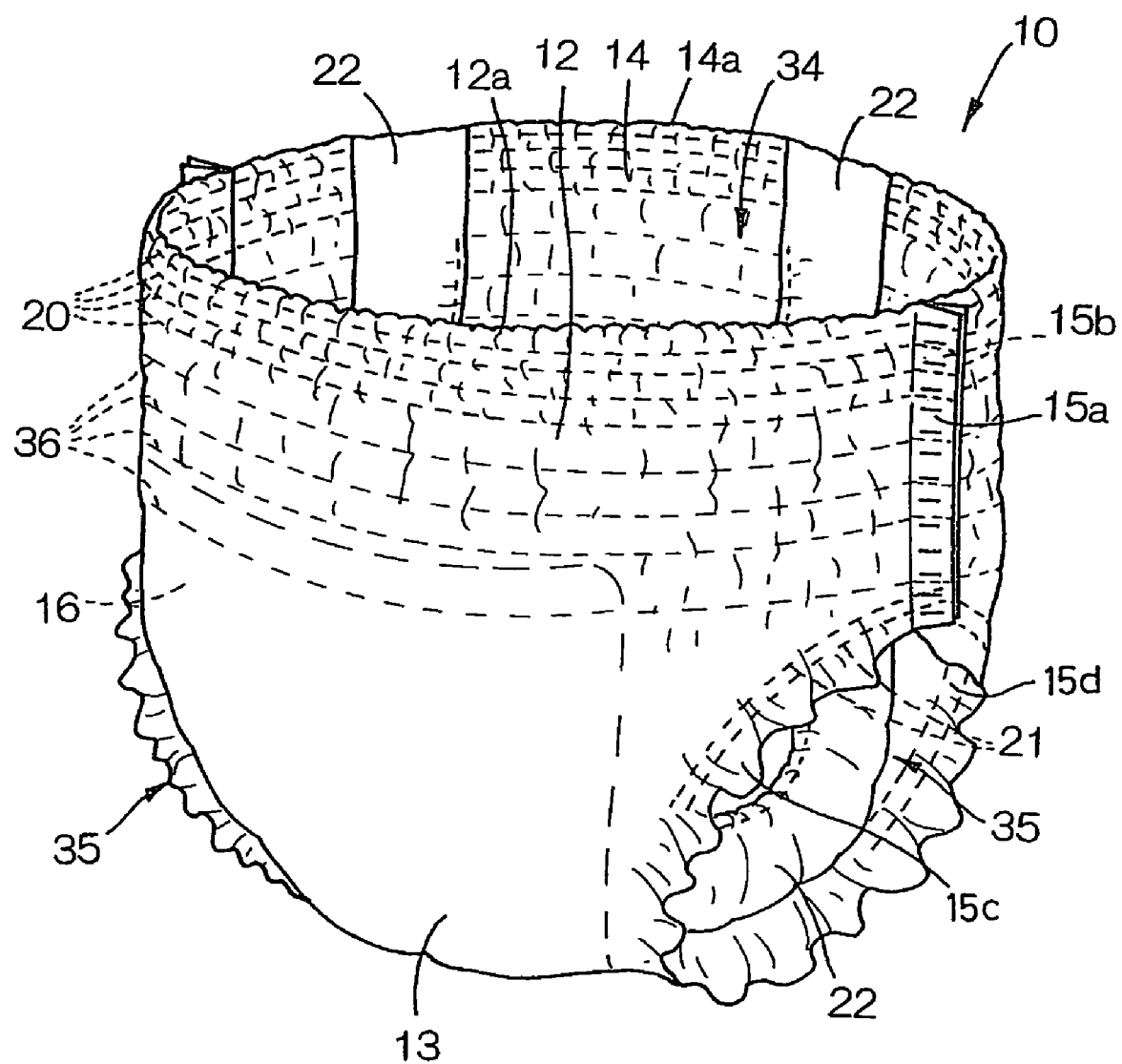
FIG. 4 is a perspective view showing a disposable diaper according to the third embodiment of this invention.
Figure 5:
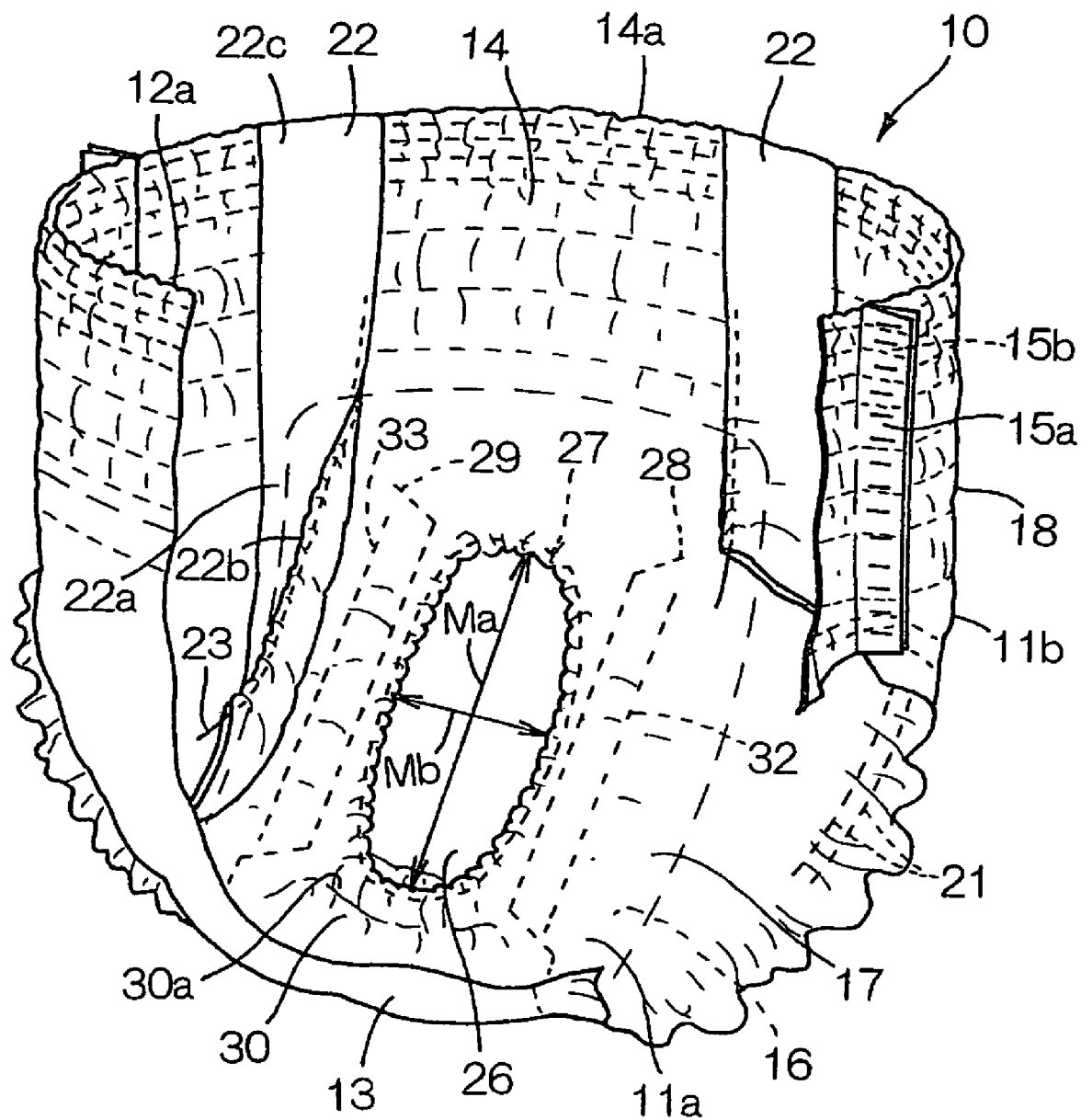
FIG. 5 is a partially cutaway perspective view of the disposable diaper shown in FIG. 4.
Figure 6:
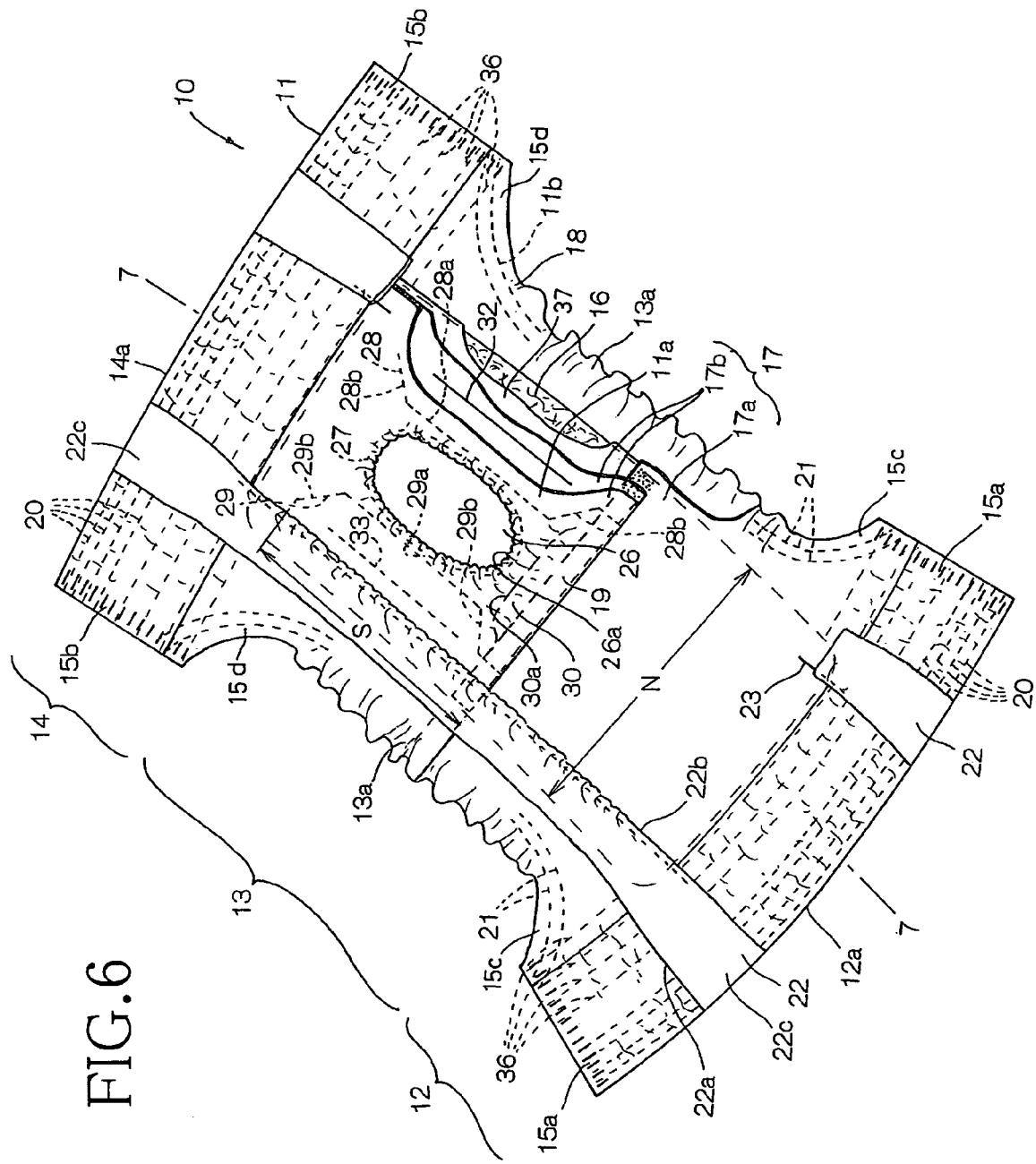
FIG. 6 is a partially cutaway plan view of the disposable diaper shown in FIG. 4 with front and rear waist regions of a chassis separated from each other along transversely opposite side edges thereof.
Figure 7:
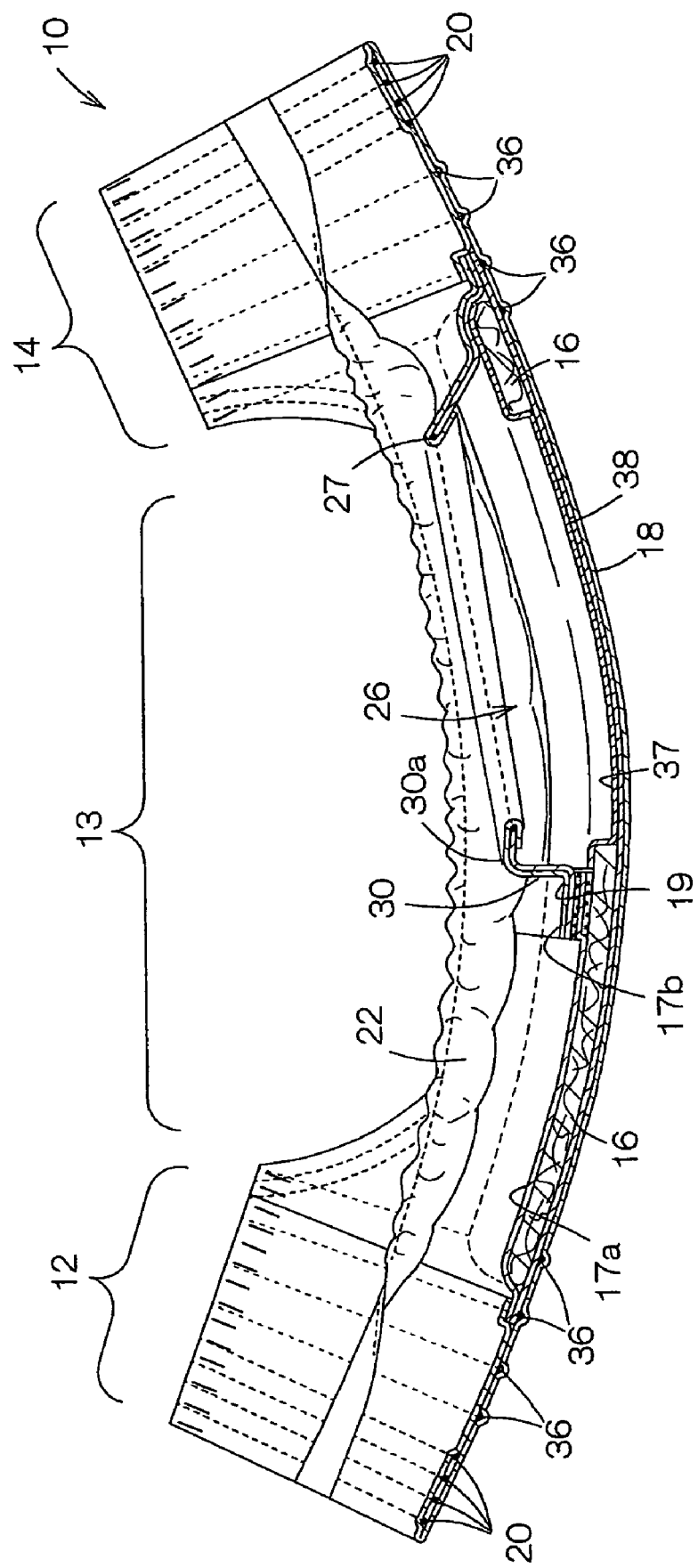
FIG. 7 is a sectional view taken along a line 7-7 in FIG. 6.

FIG. 4 is a perspective view showing a disposable pants-type (referred to also as "pull-on-type") diaper according to the third embodiment of this invention. FIG. 5 is a partially cutaway perspective view of the disposable diaper shown in FIG. 4. FIG. 6 is a partially cutaway plan view of the disposable diaper shown in FIG. 4 with front and rear waist regions of a chassis separated from each other along transversely opposite side edges thereof. FIG. 7 is a sectional view taken along a line 7-7 in FIG. 6.

Of the disposable diaper according to this third embodiment, the basic members and regions or zones similar to those in the disposable diaper according to the first embodiment are designated by the respectively corresponding reference numerals and not repetitively described.

In the disposable diaper according to this embodiment, as will be seen in FIG. 4, the front and rear waist regions 12, 14 are put flat and intermittently bonded to each other along the respective opposed side edges 15a, 15b, whereupon the disposable diaper 10 is formed with a waist-opening 34 and a pair of leg-openings 35, 35. The front and rear ends 12a, 14a of the chassis 11 are provided with a plurality of the waist-surrounding elastic members 20 laid so as to stretchable and contractible along a full circumference of the waist-opening 34 and permanently bonded to the inner surface 202 of the outer layer of the chassis 11 by means of a hot melt adhesive (not shown). A plurality of the leg-surrounding elastic members 21 are laid so as to be stretchable and contractible along the side edges 15c, 15d defining upper half circumferences of the respective leg-openings 35 and are permanently bonded to the inner surface 202 of the outer layer of the chassis 11 by means of a hot melt adhesive (not shown).

The chassis 11 is further provided on the inner surface 202 with a plurality of waist-surrounding auxiliary elastic members 36 extending so as to be stretchable and contractible in the transverse direction and spaced one from another in the longitudinal direction. Preferably, the waist-surrounding auxiliary elastic members 36 are disposed in a zone put aside from the lower ends of the respective side edges 15a, 15b toward the front and rear ends 12a, 14a (i.e., the upper ends as viewed in FIG. 4). The waist-surrounding auxiliary elastic members 36 may be a thread-like rubber made of material usually used in the industry of the disposable diaper.

The chassis 11 is additionally provided with a pair of barrier cuffs 22, 22 extending in the longitudinal direction along the opposite side edges 13a, 13a thereof. Each of these barrier cuffs 22 has a proximal section 22a, a distal section 22b and longitudinally opposite ends 22c, 22c. Immediately outside the transversely opposite edges of the absorbent panel 16, the respective proximal sections 22a, 22a are permanently bonded to the chassis 11 by means of a hot melt adhesive (not shown). The longitudinally opposite ends 22c, 22c are also permanently bonded to the chassis 11 by means of a hot melt adhesive (not shown) with the respective distal sections 22b, 22b collapsing inward in the transverse direction. The respective barrier cuffs 22 are provided with elastic members 23 for the cuffs 22 so as to be stretchable and contractible in the longitudinal direction. Contraction of these elastic members 23 causes the barrier cuffs 22 to rise up on the chassis 11 substantially in a vertical direction and serve as barriers against bodily wastes.

In the disposable diaper 10 according to this embodiment, the backsheet 18 is folded along the front and rear ends 12a, 14a of the front and rear waist regions 12, 14 back onto the inner surface 202 (See FIG. 7). The backsheet 18 includes single or plural hydrophobic thermoplastic synthetic fibrous nonwoven fabric layer or layers. An intermediate sheet 38 formed by liquid-resistant thermoplastic film is sandwiched between the backsheet 18 and the absorbent panel 16. This intermediate sheet 38 has a substantially same size as the absorbent panel 16.

The fixed zone 19 extends over a full dimension of the absorbent panel 16 in the transverse direction and, in this fixed zone 19, the first liner 17a and the second liner 17b are bonded to each other (See FIGS. 6 and 7). By dimensioning this fixed zone 19 in this manner, a bonding strength is improved.

The absorbent panel 16 includes an opening formed by partially cut out the panel 16 so that this opening in opposition to the passage 26 formed by the second liner 17b. This opening of the absorbent panel 16 and a periphery thereof are covered with a cover sheet 37 (See FIG. 7). The cover sheet 37 is preferably in close contact with the backsheet 18 inside the opening of the absorbent panel 16. In this disposable diaper 10, the internal space defined by the passage 26 is sufficiently deep to receive even relatively long feces. The cover sheet 37 may be formed by the hydrophilic sheet of prior art such as tissue paper or nonwoven fabric. In stead of using the cover sheet 37, it is possible for the equivalent effect to cover the absorbent panel 16 with the first liner 17a extending rearward from the fixed zone 19.

The second liner 17b has its front end bonded to the first liner 17a, its rear end bonded to the cover sheet 37 and its opposite side edges bonded also to the cover sheet 37. However, it is not essential that the second liner 17b is bonded along the opposite side edges thereof to the cover sheet 37 so far as the second liner 17b is bonded at least along the front and rear ends thereof to the first liner 17a or the cover sheet 37. The front end of the second line 17 lies in the fixed zone 19. While the rear end of the second liner 17b is illustrated to lie between the rear end of the absorbent panel 16 and the rear end 14a of the chassis 11, the same effect can be assured by an alternative arrangement such that the rear end of the second liner 17b falls in a line with the rear end 14a of the chassis 11 or lies in front of the rear end of the absorbent panel 16. With the arrangement that the rear end of the second liner 17b lies in front of the rear end of the absorbent panel 16, the absorbing efficiency for bodily fluid such as urine is improved. This is for the reason that bodily fluid is absorbed by the absorbent panel 16 through a region of the hydrophilic cover sheet 37 not covered with the second liner 17b. The opposite side edges of the second liner 17b lie inside the proximal sections 22a of the respective barrier cuffs 22. The liner 17b has a transverse dimension slightly smaller than that of the absorbent panel 16 while the cover sheet 37 has a transverse dimension slightly larger than that of the absorbent panel 16. In other words, the transverse dimension of the second liner 17b is smaller than that of the cover sheet 37. The disposable diaper 10 according to such embodiment ensures that, even when the second liner 17b is formed by liquid-resistant sheet material, the absorbing efficiency for bodily fluid is improved since bodily fluid is absorbed by the absorbent panel 16 through a region of the hydrophilic cover sheet 37 not covered with the second liner 17b.

Every one of the first, second and third elastic members 27, 28, 29 lies in the region of the chassis 11 in which the semi-rigid absorbent panel 16 is present (See FIG. 5). In the disposable diaper 10 of such arrangement, there is substantially no possibility that the semi-rigid absorbent panel 16 might be contracted even if movement of the wearer's body causes the waist-surrounding auxiliary elastic members 36 lying in the front and rear waist region 12, 14 of the chassis 11 to repeat stretching and contraction. Consequentially, it is unlikely that the first, second and third elastic members 27, 28, 29 lying in the region of the chassis 11 in which the semi-rigid absorbent panel 16 is present might follow such repetitive stretching and contraction of the auxiliary elastic members 36 in the transverse direction. This means that an opening dimension Mb of the passage 26 in the transverse direction substantially remains constant during use of the disposable diaper 10.

As will be apparent from FIG. 6, the paired second and third elastic members 28, 29 extend so as to be stretchable and contractible in the longitudinal direction and to describe curves which are convex toward the passage 26. In the disposable diaper 10 provided with the second and third elastic members 28, 29 of such configuration, the opening's peripheral edge of the passage 26 is normally biased by these second and third elastic members 28, 29 to be pulled outward in the transverse direction. As a result, the opening's dimension of the passage 26 in the transverse direction is always kept sufficient to guide feces reliably through the passage 26. While the second and third elastic members 28, 29 extend to the fixed zone 19 in FIG. 6, these second and third elastic members 28, 29 may further extend forward in the longitudinal direction beyond the fixed zone 19. With such unique arrangement that the second and third elastic members 28, 29 extend forward in the longitudinal direction in stretchable and contractible fashion at least to the fixed zone 19, the upper edge 30a of the rising barrier 30 can be more reliably brought in close contact with the wearer's perineum. Consequentially, feces can be reliably blocked by the barrier 30 even if feces moves forward on the wearer's skin.

The second and third elastic members 28, 29 respectively comprise intermediate rectilinear segments 28a, 29a extending in parallel to each other in the longitudinal direction and traverse segments 28b, 29b extending from longitudinally opposite ends of the respective rectilinear segments 28a, 29a so as to traverse the chassis 11 in the transverse direction. Preferably, the rectilinear segments 28a, 29a are spaced from the peripheral edge of the passage 26 in the transverse direction by 5 to 30 mm so as to intersect a line extending in the transverse direction through the longitudinal middle of the passage 26. Each of the rectilinear segments 28a, 29a preferably has a length dimension corresponding to 50 to 150% of the opening's longitudinal dimension Ma of the passage 26.

The liner 17 is further provided with paired fourth and fifth elastic members 32, 33 lying on both sides of the passage 26. More specifically, these fourth and fifth elastic members 32, 33 are put aside from the second and third elastic members 28, 29 toward the side edges of the liner 17 and sandwiched between two sheets forming the second liner 17b. These fourth and fifth elastic members 32, 33 extend substantially in parallel to each other in a stretchable and contractible fashion. By providing the disposable diaper 10 with these fourth and fifth elastic members 32, 33, the liner 17 can be more easily lifted off and the location of the passage 26 in the transverse direction can be stabilized. Preferably, the fourth and fifth elastic members 32, 33 are spaced from the peripheral edge of the passage 26 by 10 to 40 mm in the transverse direction and intersect the line extending in the transverse direction through the longitudinal middle of the passage 26. The fourth and fifth elastic members 32, 33 may be formed by thread-like or flat rubber made of the conventionally used material such as natural rubber, synthetic rubber or urethane foam just as in the case of the first, second and third elastic members 27, 28, 29.

Figure 8:
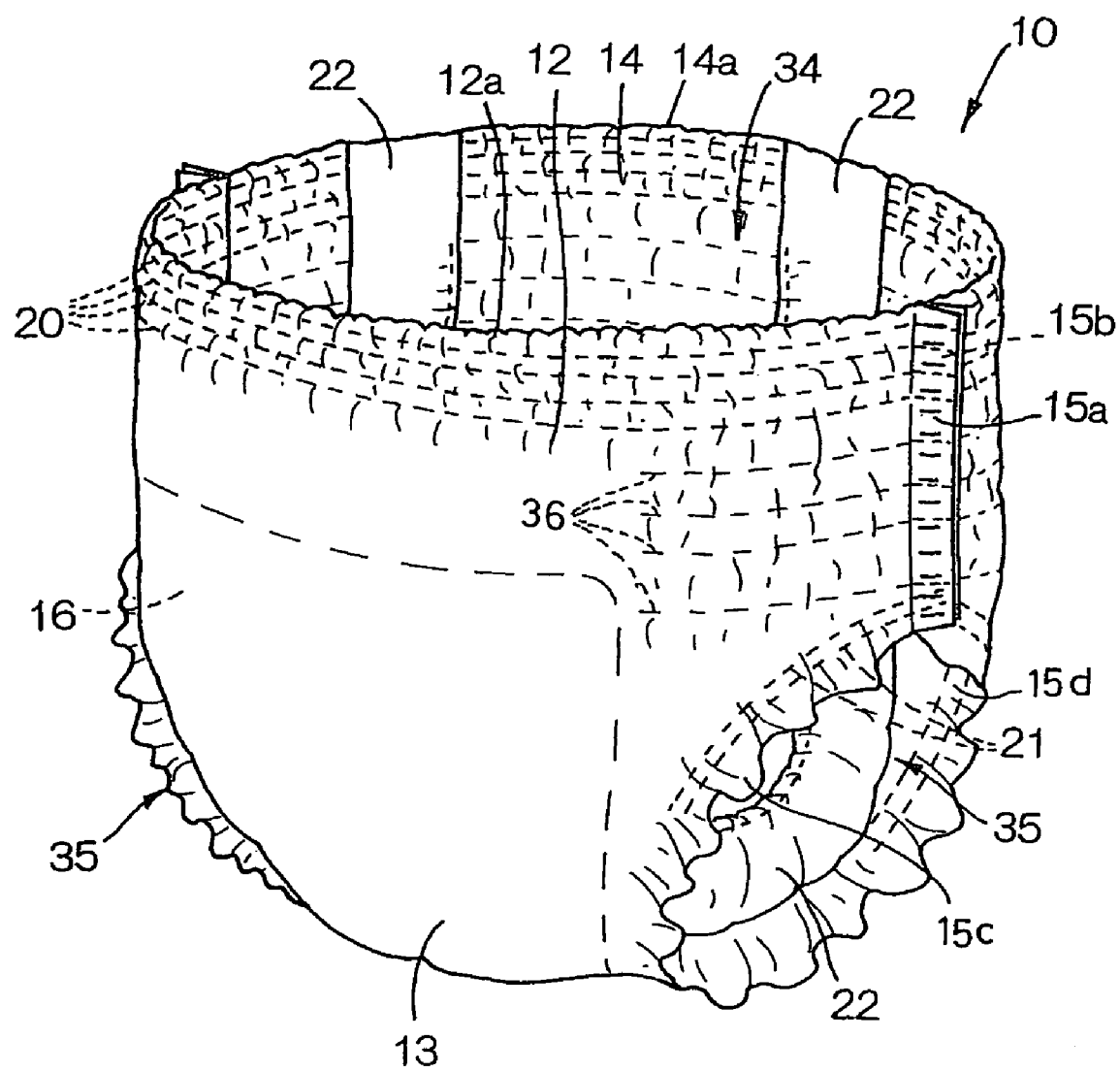
FIG. 8 is a perspective view similar to FIG. 4, showing alternative embodiment of auxiliary elastic members for waist region.

In the disposable diaper 10 according to this embodiment, the waist-surrounding auxiliary elastic members 36 function to improve fitness of the diaper 10 around the wearer's waist as has previously been described. Preferably, the waist-surrounding auxiliary elastic members 36 exhibit no stretchable and contractible elasticity in the transversely middle region of the chassis 11 in which the absorbent panel 16 is present but exhibit such elasticity in the region of the chassis 11 in which the absorbent panel 16 is absent. In order to ensure that the waist-surrounding auxiliary elastic members 36 exhibit no stretchable and contractible elasticity in the transversely middle region of the chassis 11, for example, these auxiliary elastic members 36 may be severed in the middle region or subjected to heat treatment to plasticize them or none of the waist-surrounding auxiliary elastic members 36 is laid in the middle region as illustrated in FIG. 8. Also by adjusting the rigidity of the disposable diaper 10 so as to be higher in the middle region than in the lateral regions, it is ensured that the waist-surrounding auxiliary elastic members 36 exhibit no stretchable and contractible elasticity in the middle region. In any way, the waist-surrounding auxiliary elastic members 36 may be so designed so as to exhibit neither stretchable nor contractible elasticity in the transversely middle region of the chassis 11 in order to ensure that a transverse opening's dimension Mb of the passage 26 is maintained substantially constant. In this way, a feces receiving capacity is improved while a possibility of leakage is reduced irrespectively of the wearer's posture during discharge since the opening of the passage 26 is reliably held in close contact with the wearer's anus.

What is claimed is:

1. A disposable wearing article comprising:
a longitudinal direction;
a transverse direction;
a flexible chassis having a front waist region, a rear waist region and a crotch region extending along the longitudinal direction between said front and rear waist regions;
said chassis having an outermost layer, an innermost layer, a backsheet defining said outermost layer and a liner defining said innermost layer;
a semi-rigid absorbent panel laid on an inner surface of said outermost layer;
said liner being fixed to said absorbent panel in a fixed zone which is defined substantially in a middle region of said crotch region as viewed in said transverse direction and extends in said transverse direction;
a passage formed through said liner at an area rearwardly of said fixed zone to guide feces therethrough;
a first stretchable and contractible elastic member extending along a peripheral edge of said passage; and
a second stretchable and contractible elastic member and a third stretchable and contractible elastic member which are paired and laid outside opposite side edges of said passage in said longitudinal direction in a vicinity of said passage;
wherein said second and third elastic members have end portions that are not coextensive with the first elastic member; whereby said liner is lifted off from said absorbent panel in said area so as to form a barrier rising up in the transverse direction along said fixed zone as said second and third elastic members contract,
wherein said fixed zone is elongated in the transverse direction without reaching transversely opposite edges of the crotch region of the chassis.

2. The wearing article defined by claim 1, wherein said second and third elastic members extend forward in stretchable and contractible fashion in the longitudinal direction at least to a foremost end of said passage.

3. The wearing article defined by claim 1, wherein said second and third elastic members extend forward in stretchable and contractible fashion in the longitudinal direction at least to said fixed zone.

4. The wearing article defined by claim 1, wherein said second and third elastic members extend in stretchable and contractible fashion in said longitudinal direction so as to describe curves which are convex toward said passage.

5. The wearing article defined by claim 1, wherein said liner comprises a first liner lying in a substantially front half of said chassis and a second liner lying in a substantially rear half of said chassis.

6. The wearing article defined by claim 5, wherein said second liner is liquid-resistant.

7. The wearing article defined by claim 5, wherein said first liner has a flexibility lower than that of said second liner.

8. The wearing article defined by claim 1, wherein said chassis is provided along opposite side edges the opposite side edges of the crotch region with a pair of barrier cuffs extending in said longitudinal direction.

9. The wearing article defined by claim 1, wherein said second and third elastic members extend toward the fixed zone but terminate before reaching the fixed zone.

10. The wearing article defined by claim 1, wherein the end portions of said second and third elastic members diverge from each other and away from the passage.

11. The wearing article defined by claim 1, wherein the fixed zone extends the full width of absorbent panel in the transverse direction.

12. The wearing article defined by claim 1, wherein the liner further comprises additional fourth and fifth elastic members lying on both sides of the passage, and said second elastic member and third elastic member are located between the fourth and fifth elastic members as seen in said transverse direction.

13. The wearing article defined by claim 12, said fourth and fifth elastic members extend substantially in parallel to the longitudinal direction in a stretchable and contractible fashion.

14. The wearing article defined by claim 1, wherein the liner further comprises:
a first liner laid in a front section of the chassis;
a second liner laid in a rear section of the chassis;
wherein
said first liner is located between said second liner and said absorbent panel, and
the passage is formed in the second liner but not in the first liner.

15. The wearing article defined by claim 14, further comprising, in said fixed zone, first and second discrete adhesive zones spaced from each other in the longitudinal direction, wherein
said first adhesive zone directly attaches the first liner to the second liner, and
said second adhesive zone directly attaches the second liner to the absorbent panel.

16. The wearing article defined by claim 15, wherein a section of the second liner between said first and second adhesive zones is free of direct attachment to both the first liner and the absorbent panel.

17. The wearing article defined by claim 15, wherein a thickness of the absorbent panel under the passage is greater than that under the first liner.

18. The wearing article defined by claim 1, the absorbent panel includes no absorbent material under the passage.

19. The wearing article defined by claim 1, wherein said second and third elastic member are straight throughout their entirety and said first elastic member is curved along the edge of the passage.

20. The wearing article defined by claim 10, wherein each of said second and third elastic member includes three consecutive straight portions, including a middle portion parallel with the longitudinal direction and two said end portions which extend linearly from opposite ends of the middle portions toward the front and rear waist regions, respectively, and away from the passage.

21. The wearing article defined by claim 5, wherein the first and second liners are directly bonded to each other by adhesive applied at the fixed zone.

* * * * *